United States Patent
Bowden et al.

(12) 
(10) Patent No.: US 6,374,827 B1
(45) Date of Patent: Apr. 23, 2002

(54) TRACHEO-ESOPHAGEAL TUBE AND VENTILATOR FOR PNEUMATIC CARDIOPULMONARY RESUSCITATION

(75) Inventors: Kevin D. J. Bowden, Orangeville; Tian X. Zhao, Mississauga, both of (CA)

(73) Assignee: O-Two Systems International Inc., Mississauga (CA)

( * ) Notice: Subject to any disclaimer, the term of this patent is extended or adjusted under 35 U.S.C. 154(b) by 0 days.

(21) Appl. No.: 09/412,956

(22) Filed: Oct. 5, 1999

(51) Int. Cl.[7] .............................................. A61M 16/00

(52) U.S. Cl. .................. 128/207.14; 606/192

(58) Field of Search ................................ 601/148–150; 128/207.14, 207.15; 606/192, 194

(56) References Cited

U.S. PATENT DOCUMENTS

| | | | | |
|---|---|---|---|---|
| 4,090,518 A | * | 5/1978 | Elam | 128/349 |
| 4,198,963 A | * | 4/1980 | Barkalow et al. | 128/53 |
| 4,351,330 A | * | 9/1982 | Scarberry | 128/207 |
| 4,351,342 A | * | 9/1982 | Wiita et al. | 128/349 |
| 4,497,318 A | * | 2/1985 | Donmichael | 128/20.28 |
| 4,981,470 A | * | 1/1991 | Bombeck, VI | 128/635 |
| 6,193,680 B1 | * | 2/2001 | Parsons et al. | 601/149 |

OTHER PUBLICATIONS

Krischer, Fine, Davis and Nagel, *Complications of Cardiac Resuscitaion*, Chest 1987; 92:287–291.

Kouwenhoven, W.B., Jude, J.R., Knickerbocker, G.G., *Closed–Chest Cardiac Massage*, J.A.M.A. 173: 1064, 1960; (4 pages).

Swenson, R.D., Weaver, W.D., Niskanen, R.A., Martin, J., Dahlberg, S., *Hemodynamics in Humans During Conventional and Experimental Methods of Cardiopulomonary Resuscitation*, Circulation 1998; 78:630–639.

Chandra, N., Rudikoff, M., Weisfeldt, M.L., *Simultaneous Chest Compression and Ventilation at High Airway Pressure During Cardiopulmonary Resuscitation*, Lancet 1980; 1:175–178.

Beyar, R., Kishon, Y., Dinnar, U., Neufeld, H.N., *Cardiopulmonary Resuscitation by Intrathoracic Pressure Variations—In Vivi Studies and Computer Simulation*, Angiology 1984; 35, 2:71–78.

Robotham, J.L., *Cardiovascular Disturbances in Chronic Respiratory Insufficiency*, American Journal of Cardiology 1981; 47, 4:941–949.

\* cited by examiner

*Primary Examiner*—Justine R. Yu
(74) *Attorney, Agent, or Firm*—Mark Kusner; Michael A. Jaffe

(57) ABSTRACT

The invention relates to a device for and method of cardiopulmonary resuscitation (CPR) involving cardiac compression of a patient's heart through expansion of the esophagus with an orally inserted balloon. Traditional CPR applies external pressure to the patient's sternum in an attempt to compress the heart thereby forcing blood flow through the heart. Such CPR is often ineffective or highly inefficient since the applied external force is dissipated as the force deflates the lungs and collapses the esophagus posterior the heart. The method of the invention expands the esophagus with a cyclically inflated and deflated balloon in the local area between the heart and the spine to exert a more effective local compression to the posterior of the heart. Preferably the lungs are inflated simultaneously to contain and further compress the heart during local esophageal compression. The method includes orally inserting an elongate esophageal insert having a distal tip and a proximal end to an inserted position where the tip is disposed within the esophagus posterior the heart. The insert includes an esophageal expansion balloon located on the tip for inflating and deflating the esophagus when supplied with tidal volumes of pressurized gas from an automatic cycling ventilator. The ventilator preferably is also fitted with an orally inserted tracheal tube with inflated sealing cuff to inflate the patient's lungs simultaneously with tidal volumes of pressurized gas.

6 Claims, 7 Drawing Sheets

TRACHEO-ESOPHAGEAL TUBE AND VENTILATOR FOR PNEUMATIC CARDIOPULMONARY RESUSCITATION

TECHNICAL FIELD

The invention is directed to a novel device and method of providing cardiac compression during cardio-pulmonary resuscitation (CPR) to provide the necessary cardiac output for adequate circulatory perfusion by simultaneously inflating the patient's lungs and inflating an esophageal balloon orally inserted to a position posterior the patient's heart, and including an automatic ventilator for simultaneous lung and balloon inflation.

BACKGROUND OF THE ART

Cardio-pulmonary resuscitation involves the compression of the patient's heart by application of pressure squeezing the chambers of the heart in order to maintain at least a minimal degree of blood circulation after the patient suffers a heart attack or other condition which causes the heart to cease pumping.

A conventional CPR method involves vigorously applying external pressure with the practitioner's hands to the patient's chest. A significant level of skill is required to provide consistently timed compressions of sufficient strength to compress the heart and result in adequate perfusion. This method has the advantage that a trained person can apply CPR rapidly without external equipment. However, the retention of the skill has been shown to be somewhat limited over time if the practitioner does not have an opportunity to practice often. There are significant dangers inherent in this method such as the risk of fractured ribs, internal bruising or other complications. These disadvantages are recognized in the medical literature such as for example in Krischer Fine. Davis and Nagel: "Complications of Cardiac Resuscitation" Chest 1987; 92:287–291.

A second commonly used method of cardio-pulmonary resuscitation is the direct squeezing of the heart in an internal cardiac massage. Although this method provides improved blood perfusion, compared to the above described externally applied CPR method, obviously open chest heart massage is simply not feasible in rescue or ambulance field conditions due to the need for surgical intervention. Direct heart massage therefore is limited to use as a last resort in an emergency within hospital conditions. Due to the major surgical intervention required, open chest heart massage is of extremely limited application.

The most commonly used method of CPR where external pressure is applied on the chest has been analyzed in clinical studies and is reported to generate cardiac output by compression of the heart between the posterior aspect sternum and the interior aspect of the vertebral body. The external pressure on the chest flexes the sternum and ribs toward the spine and collapses the esophagus between the posterior aspect of the heart and the spine. For example, see: Kouwnehove, W. B; Jude, J. R: Knickerbocker G. G: "Closed chest cardiac massage". J.A.M.A. 173: 1064, 1960.

Further research has put forward the conclusion that conventionally applied external cardio-pulmonary resuscitation does not generate blood flow through actual heart compression but rather increases intrathoracic pressure which generates blood flow. To date both theories remain controversial, namely whether the heart is actually compressed, or the external pressure increases intrathoracic pressure that generates blood flow independent of the heart. Further research has pursued the concept that a combination of increased intrathoracic pressure together with heart compression can be used to generate increased blood flow during CPR. Such research has been done using synchronous ventilation and externally applied cardiac compression theoretically combining these theories however with mixed results. See for example: Swenson, R. D; Weaver, W. D: Naskanen R. A., Martin. J: Dahlberg, S: "Hemodynamics in humans during conventional and experimental method of cardio-pulmonary resuscitation", Circulation 1998; 78:630–639; and Chandra. N: Rudikoff, M; Weisfeldt. M. L: "Simultaneous chest compression and ventilation at high airway pressure during CPR" Lancet 1980; 1:175–178.

Further clinical research has shown that cardiac output can be achieved by applying external pressure to the heart during lung inflation. See: Beyar R: Kishon Y: Kimmel, E: Neufeld H: Dinnar U: "Intrathoracic and abdominal pressure variations as an efficient method for CPR: studies in dogs compared with a computer model". Cardiovascular Resuscitation 1985; 19,6: 335–42; Beyar R: Kishon, Y: Neufeld, H: Dinnar, U: "CPR by intrathoracic pressure variations-in-vivo studies and computer simulation". Angiology 1984; 35, 2: 71–78; and Robotham, J. L.: "Cardiovascular disturbances in chronic respiratory insufficiency". American Journal of Cardiology 1981; 47,4:941–949.

It is an object of the invention to combine the positive aspects of the above theories and existing methods of CPR in a novel method which produces cardiac output and blood circulation during CPR in a manner with consistent results, provides improved blood perfusion, can be applied in a simple manner and is minimally invasive.

It is a further object of the invention to provide a new method of CPR with application that provides predictable consistent results independent of the particular skills of the CPR practitioner and independent of the physical characteristics of the patient.

It is a further object of the invention to provide a novel method of CPR that can be operated automatically thereby freeing paramedics to perform other necessary medical functions. In contrast, conventional CPR methods require the fall attention and both hands of the CPR practitioner.

It is a further object of the invention to provide an easily used, low cost device, which ideally includes disposable components to minimize the risk of cross-infection, and includes an automatic patient ventilation device which can be independently used for ventilation when heart operation recommences, or in other paramedic operations where cardiac arrest is not diagnosed.

Further objects of the invention will be apparent from review of the disclosure and description of the invention below.

DISCLOSURE OF THE INVENTION

The invention relates to a device for and method of cardio-pulmonary resuscitation (CPR) involving cardiac compression of a patient's heart through expansion of the esophagus with an orally inserted balloon.

Traditional CPR applies external pressure to the patient's chest at the sternum in an attempt to compress the heart thereby forcing blood flow through the heart. This prior art CPR method is often ineffective or highly inefficient since the applied external force is dissipated as the force deflates the lungs, flattens the chest cavity and collapses the esophagus posterior the heart.

The method of the invention expands the esophagus with a cyclically inflated and deflated balloon in the local area between the heart and the spine to exert a more effective local compression to the posterior of the heart. Preferably the lungs are inflated simultaneously to contain and further compress the heart during local esophageal compression.

Specifically, the method includes orally inserting an elongate esophageal insert having a distal tip and a proximal end to an inserted position where the tip is disposed within the esophagus posterior the heart. The insert includes an esophageal expansion balloon located on the tip for inflating and deflating the esophagus when supplied with tidal volumes of pressurized gas from an automatic cycling ventilator. The ventilator preferably is also fitted with an orally inserted tracheal tube with inflatable tracheal sealing cuff to simultaneously inflate the patient's lungs with tidal volumes of pressurized gas.

Further details of the invention and its advantages will be apparent from the detailed description and drawings included below.

BRIEF DESCRIPTION OF THE DRAWINGS

In order that the invention may be readily understood, one preferred embodiment of the invention will be described by way of example, with reference to the accompanying drawings wherein:

FIGS. 6A and 6B are a schematic view of the pneumatic circuits within the gas powered automatic ventilator used in association with the esophageal tube and tracheal tube to

DETAILED DESCRIPTION OF PREFERRED EMBODIMENTS

Figure 3:
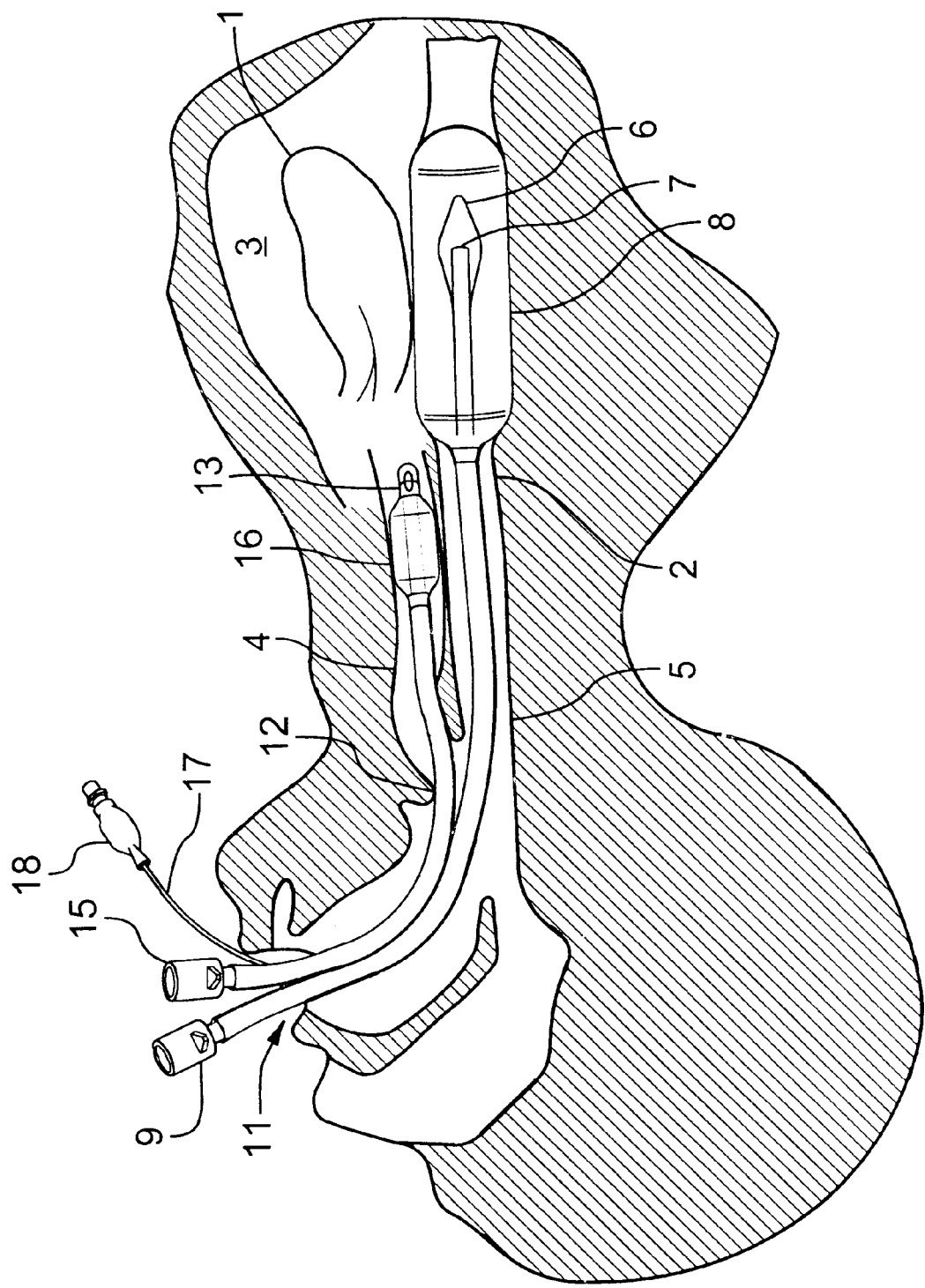
FIG. 3 is a longitudinal sectional view through a reclining patient's body showing the esophageal tube with inflated esophageal balloon posterior to the patient's heart and the tracheal tube with inflated tracheal sealing cuff surrounding the inserted end of the tracheal tube through which is conducted pressurized breathable gas in tidal volumes.
Figure 4:
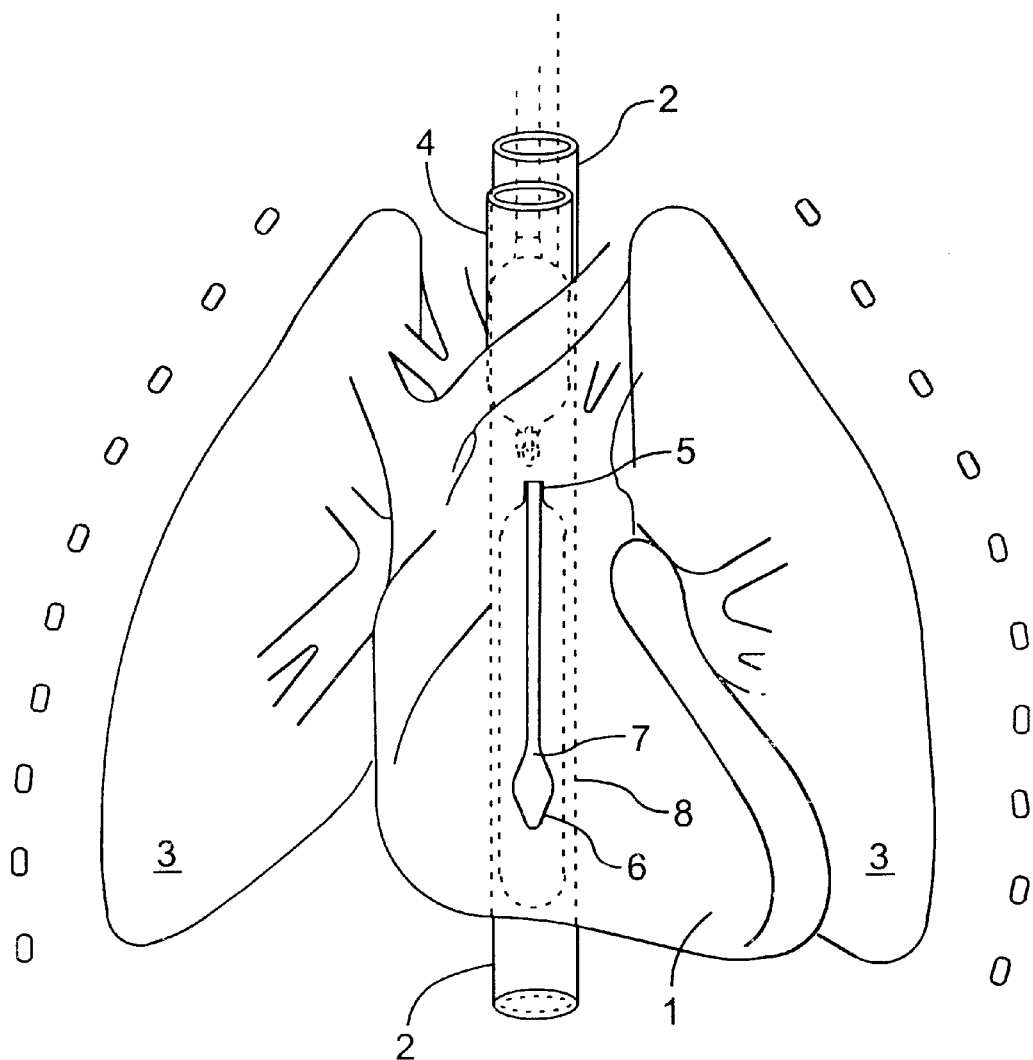
FIG. 4 is an open chest sectional view of the patient's cardio-pulmonary system with lungs deflated and esophageal balloon deflated.
Figure 5:
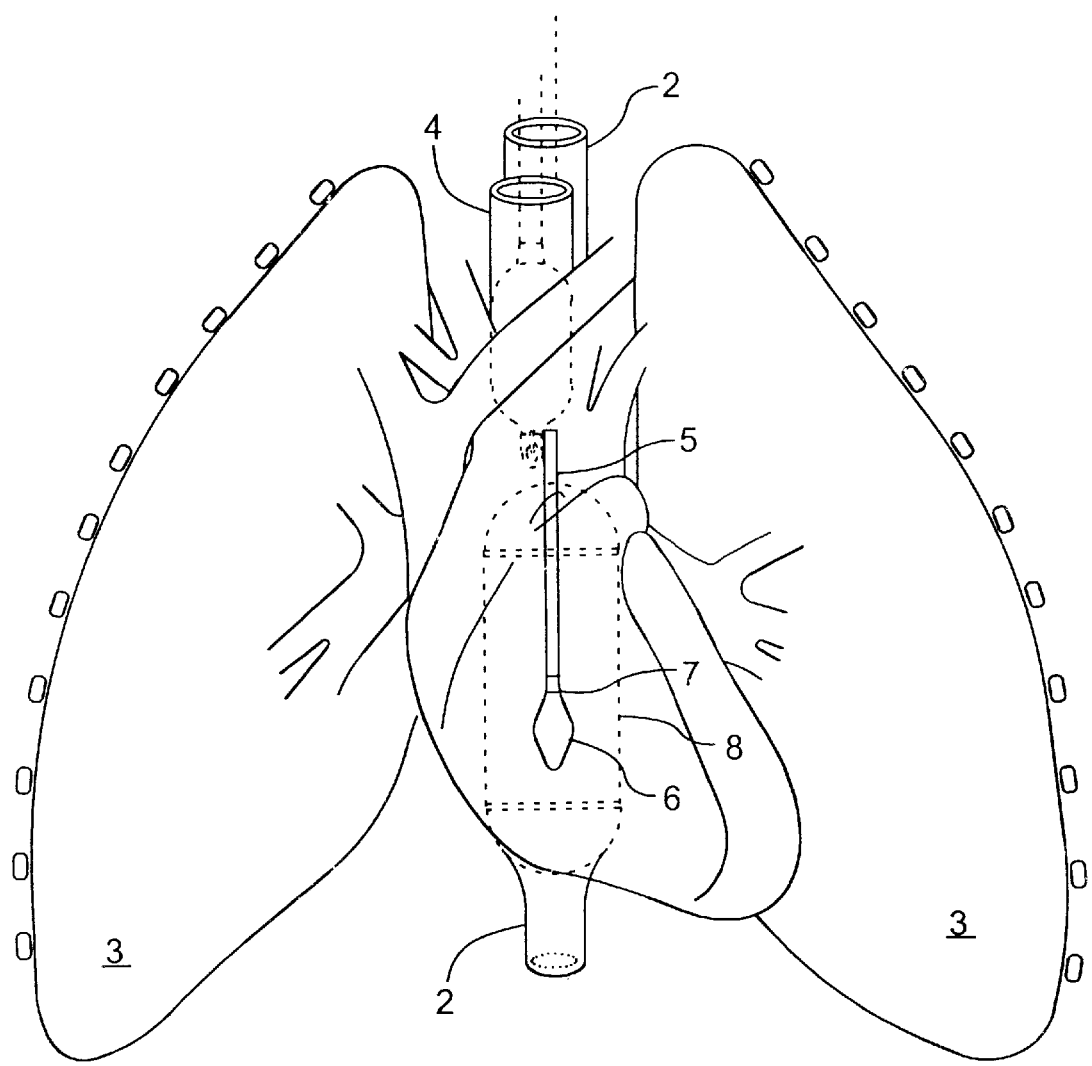
FIG. 5 is a like open chest sectional view with the esophageal balloon inflated to apply compression to the heart also with lungs inflated to apply lateral pressure to compress the heart.

Referring to FIGS. 3, 4 and 5, the invention provides a cardio-pulmonary resuscitation device for cardiac compression of the patient's heart 1 through expansion of the esophagus 2 immediately posterior the heart 1. Preferably, the method and device include means to simultaneously inflate the patient's lungs 3 such as for example by insertion of a ventilating tracheal tube through the patient's trachea 4.

FIG. 5 illustrates simultaneous inflation of the lungs 3 and the esophagus 2 with the device according to the invention whereas FIG. 4 illustrates the deflation of the esophagus and lungs thus forcing the patient's cardio-pulmonary system to inhale and exhale as well as providing cardiac compression for emergency blood perfusion.

Figure 1:
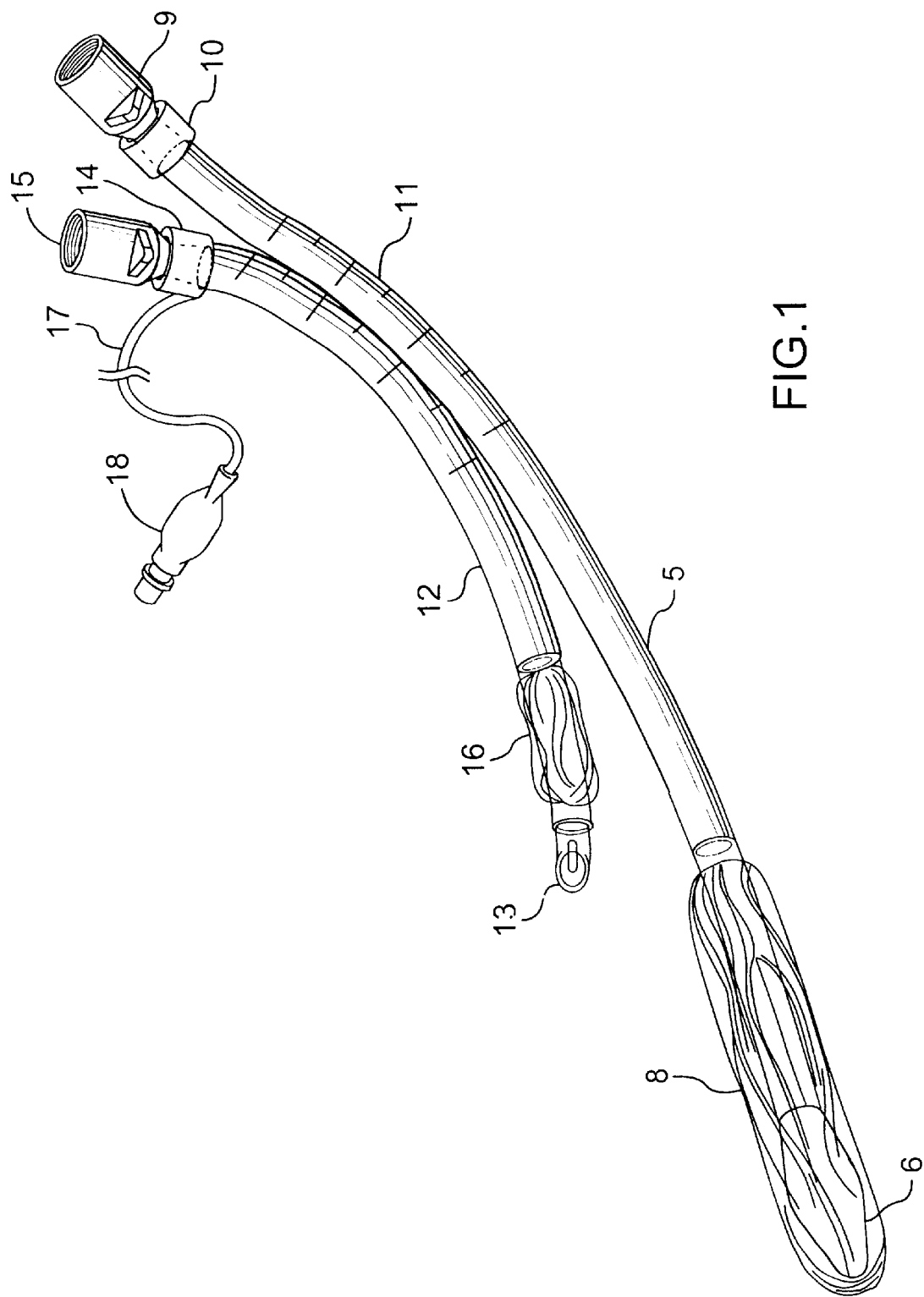
FIG. 1 is a perspective view of a combined esophageal tube (longer tube) and tracheal tube (shorter tube) the upper ends of which remain protruding from the patient's mouth with connectors for attachment to an automatic ventilator, the lower ends of which include a deflated esophageal balloon and a deflated tracheal sealing cuff respectively.
Figure 2:
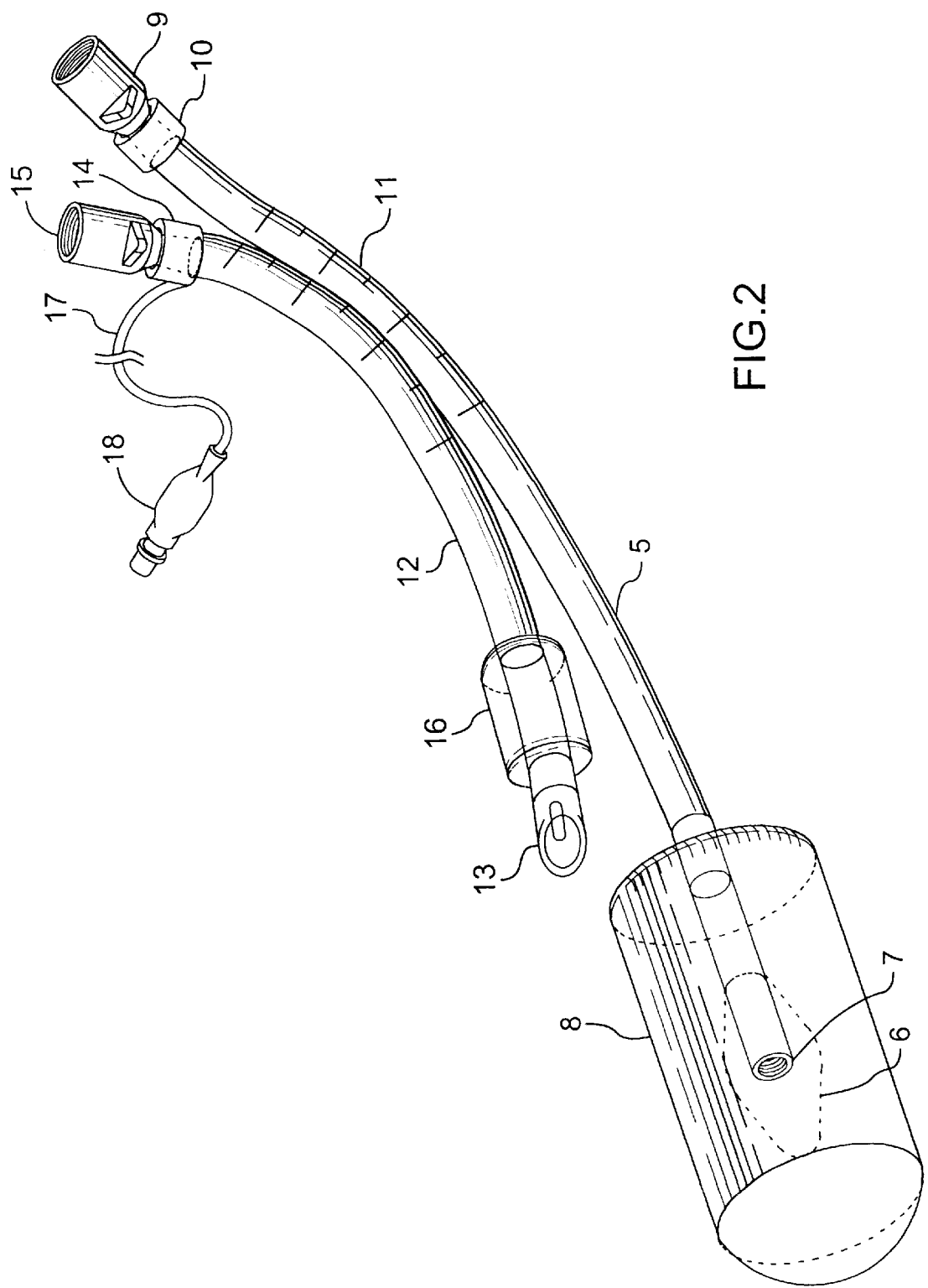
FIG. 2 is a view similar to FIG. 1 showing the esophageal balloon and the tracheal-sealing cuff fully inflated.

Referring to FIGS. 1 and 2, the details of the portions of the cardio-pulmonary resuscitation device, which are inserted into the patient's body, are described below.

The inserted portions of the resuscitation device include an elongate esophageal tube 5 with a cushioned probe 6 at the distal tip 7, in the embodiment shown disposed within an inflatable esophageal expansion balloon 8. The esophageal tube 5 includes a connector 9 at a proximal end 10 for connection to an automatic ventilator 20 that pneumatically inflates and deflates the balloon 8. As indicated in FIG. 3, the esophageal tube 5 is orally inserted using the cushioned probe 6 to guide the deflated balloon 8 to an inserted position wherein the distal tip 7 is disposed within the esophagus 2 posterior the heart 1. The ventilator 20 (described below) is thereafter connected with a hose 19 to the connector 9 and the automatic ventilator 20 provides pulses or tidal volumes of compressed gas to alternately expand and contract the balloon 8 thereby exerting local external pressure on the posterior aspect of the heart 1.

To show the depth of the tip 7 insertion within the esophagus 2, the esophageal tube 5 includes visual indicators 11 as best shown in FIG. 3. The balloon 8 when inflated serves to prevent regurgitation.

As mentioned above in respect of prior art and clinical studies, preferably the application of cardiac compression is accompanied by inflation of the patient's lungs. Whether one subscribes to the theory of improved perfusion to increase intrathoracic pressure or the theory of containing the heart laterally during localized cardiac compression, it would appear from clinical studies that improved cardiac perfusion results from simultaneous inflation of the lungs.

Accordingly, a preferred embodiment of the invention, as indicated in FIGS. 1, 2 and 3 includes a tracheal tube 12 disposed substantially parallel to the esophageal tube 5 having an insert end 13 through which breathable gas is conducted into the patient's lungs 3 from a ventilator attached with hose 19 to the protruding end 14 with ventilator connector 15. To prevent accidental misconnection, the esophageal and tracheal connectors 9 and 15 are of different sizes or styles. The tracheal tube 12 has a length adapted for oral insertion together with the esophageal tube 5 to the inserted position shown in FIG. 3. In the inserted position the insert end 13 of the tracheal tube 12 is disposed within the trachea 4 preferably below the level of the cricoid cartilage and above the carina. The visual indicators 11 on the tracheal tube 12 aid in determining proper insertion and may include markings for a variety of positions for different sized patients or children, for example.

In order to prevent the escape of breathable gas within the lungs 3, the insert end 13 of the tracheal tube 12 includes a means to pneumatically seal the trachea 4 about the tracheal tube 12. In the preferred embodiment illustrated, the pneumatic sealing device is illustrated as an inflatable cuff 16 which is inflated and deflated by pumping and exhausting air through an air supply tube 17 and a manual pump 18 with release valves in a manner similar to a commonly used blood pressure cuff and pump.

Figure 6A:
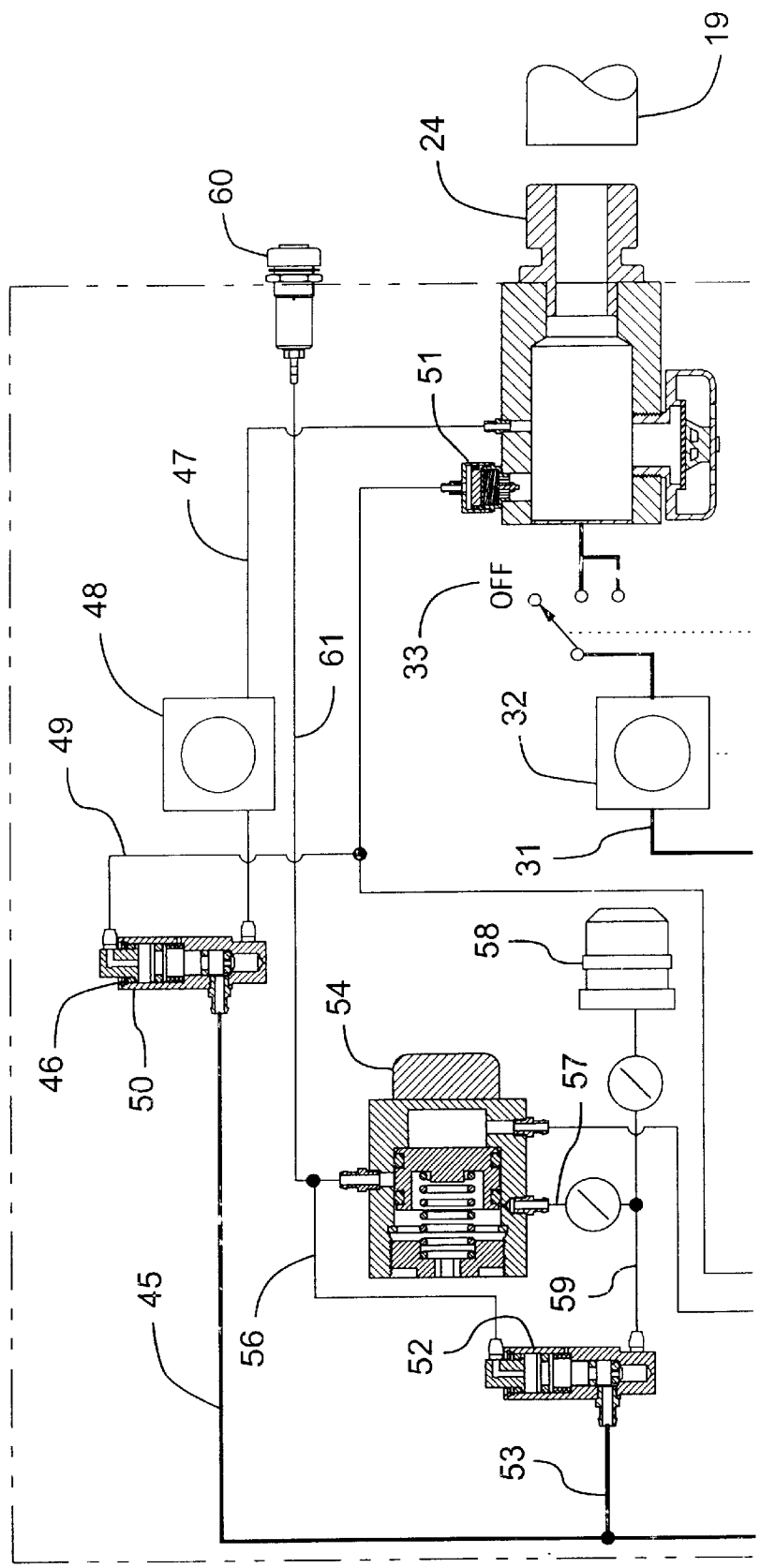
Figure 6B:
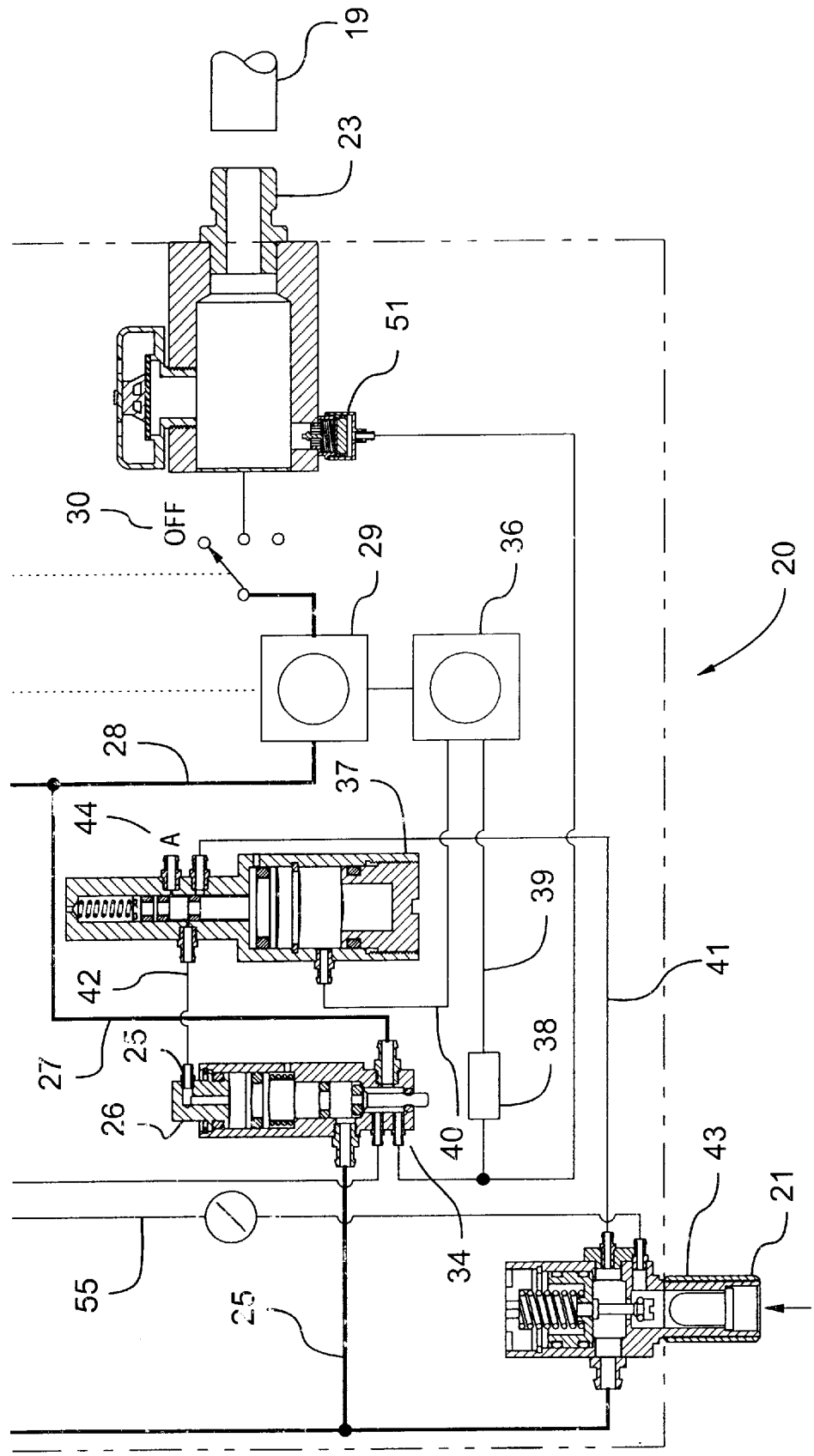

Referring to FIGS. 6A and 6B, the schematic view of an esophageal tube 5 and tracheal tube 12 is shown connected via flexible hoses 19 to an automatic ventilator 20. The inner workings of the automatic ventilator 20 will be described below.

In a preferred embodiment the ventilator 20 is a completely gas powered automatic cycling ventilator which utilizes the power from pressurized gas taken in through a pressurized gas inlet 21 as the sole means for powering the ventilator 20. In this manner, the reliance on electrical systems is eliminated. Malfunctioning batteries, short-circuits, explosion hazards, and other common problems with electrically powered ventilators are avoided.

The automatic ventilator 20 includes a internal pressure regulator 22 immediately downstream of the pressurized gas inlet 21 to provide the precise control over the gas pressure required for automatic ventilator applications. The automatic ventilator 20 includes an esophageal tube outlet port 23 and a tracheal tube outlet port 24.

In operation, therefore the method of cardio-pulmonary resuscitation according to the invention proceeds as follow. Referring to FIG. 3, after diagnosing cardiac arrest in the patient the paramedic orally inserts the elongate esophageal tube 5 using a laryngoscope to observe the pharynx and the esophageal opening. The esophageal tube 5 and tracheal tube 4 are gradually inserted into the patient's mouth and the tip 7 of the longer esophageal tube 5 is guided with the cushioned probe 6 down the esophagus 2. Under direct visualization through the laryngoscope, the esophageal tube 5 continues to be inserted until the insert end 13 of the tracheal tube 12 lies opposite the larynx. Both tubes 5 and 12 are further inserted until the tracheal tube 12 is positioned with insert tip below the level of the cricoid cartilage but above the carina, and the esophageal balloon 8 in a deflated state as shown in FIG. 1 is positioned posterior the patient's heart I as shown in FIG. 3.

The curvatures of the tubes 5 and 12 as shown in FIGS. 1 and 2 are preferably designed to mimic the internal geometry of the human oro-pharynx to allow for easy insertion into the esophagus 2 and trachea 4 as shown in FIG. 3. The tubes 5 and 12 are joined together for a distance of approximately 4 inches near the connectors 9 and 15 and bifurcate distally at an angulation to allow for an anatomical fit within the oropharynx once the tubes 5, 12 are fully inserted to reduce the risks of kinking and tube blockage.

Once inserted as illustrated in FIG. 3, the paramedic manually squeezes the flexible pump 18 to inflate the cuff 16 with air delivered via the air supply tube 17 to seal the trachea 4. Thereafter, the connectors 9 and 15 are connected via flexible hoses 19 to the outlet ports 23 and 24 of the automatic ventilator 20.

The automatic ventilator 20 delivers pulses of compressed gas tidal volumes through the esophageal tube outlet port 23 to selectively expand and contract the esophageal balloon 8. Balloon 8 inflation applies pressure to the posterior aspect of the heart 1 and the heart 1 compresses within the thoracic cavity against the posterior aspect of the sternum. The balloon 8 inflation pressure is directed interiorly and laterally by the presence of a large vertebral body posterior the esophagus 2.

Therefore, due to the anatomy of the esophagus 2 and vertebrae, the inflating and deflating balloon 8 is able to rhythmically exert local pressure on the heart 1 in a manner significantly superior to externally applied pressure on the sternum and rib cage. In addition, the automatic ventilator 20 provides control over the process which can be repeated, clinically proven and rendered highly predictable. The automatic ventilator 20 frees the paramedic to attend to other emergency requirements.

In a preferred embodiment, the automatic ventilator 20 also provides pulses of tidal volumes of compressed breathable gas to inflate the patient's lungs via the inserted end 13 of the tracheal tube 12. As presently contemplated by the inventors, the preferred method includes inflating the patient's lungs with pressurized gas simultaneously with the pneumatic inflation of the esophageal balloon 8, however clinical trials may show that other timing sequences are effective as well. The inflated lungs simultaneously compress the heart 1 laterally. This improved compression of the heart is sufficient to cause blood to be squeezed out of the heart and recirculated around the body. Oxygenation of the circulated blood takes place simultaneously due to the ventilation of breathable gas within the lungs 3.

Between simultaneous pulses or tidal volumes of pressurized gas, the expiratory phase of operation permits the balloon 8 to deflate and lungs 3 to simultaneously deflate allowing the heart 1 to rebound and refill with blood ready for the next pulse or compression.

The automatic ventilator can be designed to provide simultaneous inflation of the lungs 3 and esophageal balloon 8 or can be designed to provide a delay between lung inflation and heart compression. The automatic ventilator 20 can also be designed to rapidly pulse at speeds which are not attainable through manual CPR methods.

It will be apparent as well that once the paramedic inserts the device and commences operation of the automatic ventilator 20, the paramedic is free to attend to the other needs of the patient while visually monitoring the automatic ventilator. It will also be apparent that once the paramedic detects that the patient's heart 1 has recovered and commences pumping blood, the automatic ventilator 20 can be designed to cease operation of the balloon 8 and operate solely as a patient ventilator providing tidal volumes of the breathable gas through the tracheal tube 12.

Turning th FIGS. 6A and 6B, the details of 1 preferred embodiment of the automatic ventilator 20 will be described. As previously mentioned, the preferred embodiment includes a gas powered automatic ventilator 20 independent of electrical controls or any other power or control source apart from the supply of pressurized gas through the pressurized gas inlet 21.

An automatic circuit communicates between the pressurized gas inlet 21 and each of the outlet ports 23 and 24 for simultaneous automatic inflation of the esophageal balloon 8 via the esophageal tube 5 and the patient's lungs 3 via the tracheal tube 12. The automatic circuit is supplied with pressurized gas from the inlet 21 via an automatic supply conduit 25 to a main on/off valve 26. Output from the main valve 26 continues along conduit 27.

An automatic esophageal output conduit 28 conducts pressurized gas between the main valve 26 and the esophageal outlet port 23 through the esophageal flow control valve 29 and mode switch 30. Simultaneously, an automatic tracheal output conduit 31 conducts pressurized gas from the main valve 26 through the tracheal output port 24 through the tracheal flow control valve 32 and mode switch 33. Mode switches 30 and 33 are illustrated in the OFF position wherein gas flow is prevented from proceeding to the ports 23 and 24. When switches 30 and 33 are simultaneously rotated clockwise to a dual flow position, gas is simultaneously conveyed to the esophageal outlet port 23 from the esophageal output conduit 28 and to the tracheal outlet port 24 through the tracheal output conduit 31. Further clockwise rotation of the switches 30 and 33 to a ventilation only position prevents flow to the esophageal outlet port 23, while maintaining flow through the tracheal outlet port 24 in order to cease inflation and deflation of the balloon 8 while maintaining automatic ventilation through the tracheal tube 12 to the patient's lungs 3.

The flow control valves 29 and 32 provide restriction of the passage of pressurized gas preferably by passing the pressurized gas through laser drilled holes in an indexable rotating disc. The disc is indexed between different sized of laser drilled holes to precisely determine the restriction opening and ensure precise control over the flow delivered through the valves 29 and 32.

The automatic circuit also includes an automatic timing circuit which communicates between a bleed 34 downstream the main valve 26 and a main valve control chamber 35 via a frequency control valve 36 and a timing switch 37. The timing of automatic pressurized gas pulses is provided as follows. To commence operation of the automatic circuit, the paramedic operator turns the switches 30 and 33 to one of the operating positions and opens a valve on a breathable gas cylinder (not illustrated) to deliver pressurized gas to the pressurized gas inlet 21. The main valve 26 is spring-loaded normally open and pressurized gas continues through conduits 25, 27, 28, 31, and hoses 19 to simultaneously pressurise the patient's airway and the inflatable balloon 8. When the main valve 26 is an open position, a small amount of pressurized gas also proceeds through bleed 34, filter 38 and conduit 39 to the frequency control valve 36. The frequency control valve 36 resists the passage of pressurized gas preferably through restriction of an opening in an indexable laser drilled plastic disc. Pressurized gas proceeds through the frequency control valve 36 and conduit 40 to a control chamber of the timing switch 37. When the volume of gas proceeding through the frequency control valve 36 is adequate to pressurise the control chamber of the timing switch 37, the switch is activated to move from a inhale position to an exhale position. In the exhale position, pressurized gas can proceed from the regulator 40 through conduit 41 through the stem of the timing switch 37 to conduit 42 to pressurise the chamber 25 within the main valve 26 and close the main valve 26.

When the main valve 26 is open, gas conveyed from bleed 34 maintains anti-lockup valves 51 closed. Over time, a sufficient amount of gas also passes through bleed 34, conduit 39, to frequency control valve 36, to pressurize the control chamber of timing switch 37 and overcome the biasing force of a spring keeping the timing switch 37 normally in the inhale position. At this stage the timing switch 37 is shifted to an exhale position wherein gas is vented through conduit 42 from the main valve 26 to atmosphere via vent 44.

When the main valve 26 is closed, the anti-lockup valves 51 vent pressurized gas from the tracheal port 24 and the esophageal port 23 to atmosphere. Pressurized gas within the control chamber of the timing switch 37 also slowly vents to atmosphere backwards through conduit 40, frequency control valve 36, conduit 39 to bleed 34, conduit 27 and ports 23, 24. In this manner, the cycling of the timing switch 37 serves to open and close the main valve 26 in a precisely controlled predictable manner.

The automatic ventilator 20 also preferably includes a continuous patient airway pressure circuit communicating between the pressurized gas inlet 21 and the tracheal outlet port 24 for maintaining gas pressure within the tracheal tube 12 and the patient's lungs 3 at above a selected minimum CPAP pressure when the automatic circuit main valve 26 is closed. The CPAP pressure is supplied by a CPAP supply conduit 45 delivering gas to the CPAP valve 46. The CPAP output conduit 47 conducts pressurized gas between the CPAP valve 46 and the tracheal outlet port 24 through the CPAP control regulator 48. The CPAP valve control conduit 49 communicates between the bleed 34 downstream of the main valve 26 and a CPAP valve control chamber 50.

In operation, when the main valve 26 is open, a supply of pressurized gas escapes from the bleed 24 via conduit 49 to pressurise the CPAP valve control chamber 50 and close the CPAP valve 46. When the timing switch 37 closes the main valve 26, the CPAP valve control chamber 50 slowly vents through bleed 34, conduit 27, ports 23, 24 and anti-lockup valves 51. When the CPAP valve control chamber 50 is vented to a sufficient degree, pressure drops within the chamber 50 and is insufficient to resist biasing force of a spring within the CPAP valve 46 that maintains the CPAP valve 46 normally open. The CPAP valve 46 opens delivering pressurized gas from the CPAP supply conduit 45 via conduit 47 to the tracheal tube outlet port 24. CPAP control regulator 48 provides flow restriction to control the pressurisation of the tracheal outlet port 24 during exhale stage of the ventilation cycle.

The ventilator 20 also includes an alarm circuit in communication with the pressurized gas inlet 21 for initiating an alarm when the inlet gas pressure is below a selected minimum alarm pressure. An alarm valve 52 is supplied with pressurized gas via conduit 53. Pressure sensing valve 54 is provided with unregulated supply gas direct from the gas inlet 21 (bypassing regulator 43) via conduit 55 to close valve 54 by pressurizing a control chamber against the pressure of a spring keeping the valve 54 in a normally open position. Pressurized gas passes through the control chamber of valve 54 from conduit 55 to conduit 56 to pressurized and close the (spring-loaded normally open) alarm valve 52. When the pressure of gas provided through conduit 55 is below a selected alarm pressure, the spring within pressure sensing valve 54 forces a piston within valve 54 to exhaust gas from the alarm valve 52 through conduit 56 to conduit 57 and reed alarm 58. When pressurized gas from the normally open alarm valve 52 is released, the valve 52 opens and further gas is supplied through conduit 53 and conduit 59 to sound the reed alarm 58. By this means, the operator is given notice when the supplied pressurized gas becomes depleted or obstructed through the means of audible reed alarm 58. Optionally, a visual pop-indicator 60 supplied via conduit 61 can also be used visually indicate the state of inlet pressure.

Although the above description and accompanying drawings relate to a specific preferred embodiment as presently contemplated by the inventors, it will be understood that the invention in its broad aspect includes mechanical and functional equivalents of the elements described and illustrated.

The embodiments of the invention in which an exclusive property or priviledge is claimed are defined as follows:

1. A cardio-pulmonary resuscitation device for cardiac compression of a patient's heart through expansion of the esophagus adjacent to the heart and simultaneous inflation of the patient's lungs, the device comprising:

an elongate esophageal insert having a distal tip and a proximal end, the insert having a length adapted for oral insertion of the tip to an esophageal inserted position wherein the tip is disposed within the esophagus posterior the heart;

esophageal expansion means located on the distal tip of the esophageal insert for compressing the patient's heart between an anterior of the patient's expanded esophagus and a posterior of the patient's sternum by expanding the esophagus when in the inserted position and for releasably sealing the esophagus against aspiration of stomach contents and regurgitation;

a tracheal tube disposed substantially parallel the esophageal insert and having an insert end and a protruding end, the tracheal tube having a length adapted for oral insertion together with the esophageal insert to a tracheal inserted position wherein the insert end of the tracheal tube is disposed within the trachea, wherein the insert end includes pneumatic sealing means for releasably sealing the trachea about the tracheal tube; and control means in communication with the esophageal expansion means and with the tracheal tube, for selectively expanding and contracting the esophageal expansion means and simultaneously inflating and deflating the lungs of the patient via the tracheal tube sealed within the trachea of the patient.

2. A cardio-pulmonary resuscitation device according to claim 1 wherein the esophageal expansion means comprise an inflatable balloon, the esophageal insert comprises an esophageal tube in communication with the balloon and wherein the control means include pneumatic inflation means in communication with the proximal end of the esophageal tube for selectively inflating and deflating the balloon.

3. A cardio-pulmonary resuscitation device according to claim 2 wherein the distal tip of the esophageal tube includes a cushioned probe disposed within the balloon.

4. A cardio-pulmonary resuscitation device according to claim 2 wherein the esophageal tube includes visual indicators along its length to indicate the depth of tip insertion within the esophagus.

5. A cardio-pulmonary resuscitation device according to claim 1 wherein the pneumatic sealing means comprise an inflatable cuff.

6. A cardio-pulmonary resuscitation device according to claim 1 wherein the tracheal tube includes visual indicators along its length to indicate the depth of insert end insertion within the trachea.

* * * * *